US006854973B2

(12) United States Patent
Butcher et al.

(10) Patent No.: US 6,854,973 B2
(45) Date of Patent: Feb. 15, 2005

(54) METHOD OF WET-FIELD SCANNING

(75) Inventors: Nancy Butcher, Dallas, TX (US);
Friedrich Riemeier, Berlin (DE);
Gregg Cohen, Frisco, TX (US)

(73) Assignee: OraMetrix, Inc., Richardson, TX (US)

( * ) Notice: Subject to any disclaimer, the term of this patent is extended or adjusted under 35 U.S.C. 154(b) by 199 days.

(21) Appl. No.: 10/099,042

(22) Filed: Mar. 14, 2002

(65) Prior Publication Data

US 2003/0175658 A1 Sep. 18, 2003

(51) Int. Cl.[7] ................................. A61C 3/00
(52) U.S. Cl. ..................................... 433/214; 433/229
(58) Field of Search ........................ 433/29, 213, 214, 433/215, 218, 229

(56) References Cited

U.S. PATENT DOCUMENTS

| | | | |
|---|---|---|---|
| 4,837,732 A | | 6/1989 | Brandestini et al. ... 364/413.28 |
| 5,027,281 A | | 6/1991 | Rekow et al. ......... 364/474.24 |
| 5,266,030 A | * | 11/1993 | Van Der Zel ................. 433/68 |
| 5,338,198 A | | 8/1994 | Wu et al. .................... 433/213 |
| 5,372,502 A | | 12/1994 | Massen et al. .............. 433/215 |
| 5,386,292 A | * | 1/1995 | Massen et al. .............. 356/603 |
| 5,554,028 A | * | 9/1996 | Hare et al. .................. 433/214 |
| 5,897,696 A | * | 4/1999 | Giordano et al. ............. 106/35 |
| 5,944,521 A | * | 8/1999 | Lawler ......................... 433/88 |
| 6,099,313 A | * | 8/2000 | Dorken et al. .............. 433/175 |
| 6,386,867 B1 | * | 5/2002 | Durbin et al. ................ 433/31 |

FOREIGN PATENT DOCUMENTS

| | | | |
|---|---|---|---|
| EP | 0 234 422 | * | 9/1987 |
| WO | WO 98/48242 | * | 10/1998 |
| WO | WO 0180761 | | 11/2001 |
| WO | WO 0184479 A1 | | 11/2001 |

OTHER PUBLICATIONS

Yee et al., *Three-dimensional Imaging System, Optical Engineering*, vol. 33, No. 6, Jun. 1994, pp. 2070–2075.

S.M. Yamany and A.A. Farag, "A System for Human Jaw Modeling Using Intra-Oral Images" in *Proc. IEEE Eng. Med. Biol. Soc. (EMBS) Conf.*, vol. 20, Hong Kong, Oct. 1998, pp. 563–566.

S.M. Yamany, A.A. Farag, David Tasman, A.G. Farman, "A 3-D Reconstruction System for the Human Jaw Using a Sequence of Optical Images," *IEEE Transactions on Medical Imaging*, vol. 19, No. 5, May 2000, pp. 538–547.

Dianne Rekow, "*Computer-aided design and manufacturing in dentistry*" *A review of the state of Art,* Journal of Prosthetic Dentistry, vol. 58, No. 4 (Oct. 1987).

PCT International Search Report for OraMetrix, Inc., PCT/US03/03825, dated Dec. 24, 2003.

* cited by examiner

*Primary Examiner*—Ralph A. Lewis
(74) *Attorney, Agent, or Firm*—McDonell Boehnen Hulbert & Berghoff LLP

(57) ABSTRACT

A method is provided for scanning the surface of an object in which moisture such as saliva or water is present on the surface. The method includes the step of applying a saliva and water-resistant composition to the surface, wherein the composition is characterized in that it does not readily wash off the surface after application of the composition to the surface in the presence of saliva or water. The composition forms an opaque film on the surface. The method further includes the step of scanning the surface having the film with a scanner. Several formulations for the composition are disclosed. One includes a liquid alcohol base, such as dehydrated ethyl alcohol, a reflective pigment, and a binder for promoting good adhesion of the formulation to the surface of the object being scanned. A suitable binder for scanning teeth and other oral structures is a denture adhesive such as an off-the-shelf denture adhesive, in powder form, that is mixed with the pigment and the alcohol base. Other suitable compositions can be derived by persons skilled in the art from the teachings disclosed herein.

14 Claims, No Drawings

METHOD OF WET-FIELD SCANNING

BACKGROUND OF THE INVENTION

A. Field of the Invention

This invention relates generally to the subject of three-dimensional scanners, for example those based on projection of a two-dimensional coded pattern off of a surface and capture of the reflected pattern. More particularly, the invention relates a method of scanning an object in a "wet-field" environment, that is, where the object to be scanned is moist with water or saliva. One example is oral structures, such as teeth, lips and gingival tissue, in a human patient. The method involves applying a composition of matter to the surface that improves the reflective properties of the object and temporarily resists being washed away from the surface due to the presence of water, saliva, or other moisture.

B. Description of Related Art

Three-dimensional scanners for scanning of teeth (either directly or from a model) are known in the art and described in the patent literature. See the published PCT patent application of OraMetrix, Inc., publication no. WO 01/80761, the entire contents of which are incorporated by reference. See also Rekow, et al., U.S. Pat. No. 5,027,281, Massen et al., U.S. Pat. No. 5,372,502 and Brandestini et al., U.S. Pat. No. 4,837,732.

The scanner of WO 01/80761 uses a coded projection pattern consisting of a two dimensional array of lines and colored dots. The pattern is projected onto the surface to be scanned. The pattern is reflected off of the surface and imaged by a two dimensional charge coupled device (CCD) chip. The location of where the various portions of the projected pattern is imaged by the CCD chip contains information as to the three-dimensional location of the points on the object's surface corresponding to points in the reflected pattern. An algorithm derives 3D location information for all the available points in the reflected projected pattern, thus deriving 3D information as to the surface being scanned.

Some surfaces have an inherent reflectivity such that the projected pattern from a scanner such as described in WO 01/80761 will reflect the projected pattern onto the imaging device to a satisfactory degree without any prior preparation of the surface. Other surfaces are relatively non-reflective or translucent, or otherwise do not reflect the projected pattern to a sufficient degree. For such surfaces, the scanning of the object can be improved by applying a substance to the object to improve its reflective properties. The CEREC scanning device developed by Brandestini et al. is used in conjunction with a $TiO_2$-based aerosol powder which is applied to the teeth.

When the object is being scanned is the teeth, lips, or other oral structures of a human patient, particular problems arise that have not been satisfactorily addressed by the prior art. For example, the $TiO_2$-based aerosol powder used in the CEREC system tended to form small globules on the surface of the teeth, which interferes with obtaining accurate 3D surface information. The formulation was readily washed away by saliva. It did not adhere well to the tooth surface. Moreover, the powder was also quite technique sensitive and difficult to apply evenly, in that the ability to apply the power evenly and spread it over the entire surface of the tooth was dependent to a large degree on the skill of the operator. While the powder could be used by a very skilled operator for very limited scanning of a single tooth (with adequate saliva-absorbing material completely surrounding the tooth) in a dry field environment, it is completely inadequate for scanning a set of teeth or an entire jaw, a situation in which the required dryness cannot be practically achieved in any convenient fashion.

SUMMARY OF THE INVENTION

A method is provided for scanning the surface of an object in which moisture such as saliva or water is present on the surface. The method is suitable for use in scanning larger objects besides a single tooth, such as an entire arch and associated gingival tissue, in a wet field environment. The method includes the step of applying a saliva and water-resistant composition to the surface, wherein the composition is characterized in that it does not readily wash off the surface after application of the composition to the surface in the presence of saliva or water. The composition preferably dries to a film covering the surface which is substantially opaque or otherwise improves the reflective properties of the surface. The method further includes the step of scanning the surface having the composition applied thereto. The composition thus improves the ability of the scanner to project a coded projection pattern onto the surface of the object and capture the reflected projection pattern.

Several suitable formulation for a wet-field opaquing composition are disclosed. One is a liquid composition which includes a liquid alcohol base, such as dehydrated ethyl alcohol, a reflective pigment, and a binder for promoting good adhesion of the formulation to the surface of the object being scanned. A suitable binder for scanning teeth and other oral structures is a denture adhesive such as an off-the-shelf denture adhesive, in powder form, that is mixed with the pigment and the alcohol base. Other suitable compositions can be derived by persons skilled in the art from the teachings disclosed herein. The invention also contemplates the use of aerosol or powdered compositions that have good adhesion to surfaces in a wet-field environment, such as a powdered composition comprising a binder and a pigment. After the composition is applied to the surface of the object in the wet-field environment, the composition is preferably allowed to dry to a film covering the surface and the surface is scanned.

In one possible application of the invention, a method of in-vivo scanning of an anatomical structure of a human is provided in a wet-field environment, comprising the step of: applying a biocompatible, saliva and water-resistant composition to the surface of the anatomical structure. For example, the composition may comprises a base, a pigment and a binder composed of a material having a tendency to harden or become sticky in the presence of water or saliva and thereby not be washed off the surface of the anatomical structure. The method continues with the steps of allowing the composition to dry to a film covering the surface of the anatomical structure with the film improving the opacity of the surface, and scanning the surface having the film with a scanner.

The present invention provides methods which are particularly well suited for scanning in-vivo oral structures, including teeth, a set of teeth, the entire upper and/or lower jaw, lips, and/or gingival tissue, or other anatomical structures, in a wet-field environment. It can be used to scan orthodontic and dental appliances and devices, such as orthodontic brackets, crowns, and other devices. It could also conceivably be used in dry-field environments and used to improve the scanning of the object. Finally, while the method is particularly useful for scanning based on projection of two-dimensional coded patterns, it can be used in other types of scanning systems and the invention is certainly not limited to use in a scanner described in the above-referenced patent documents. Rather, it is ideally suited to any type of scanning in which a specific non-transparent surface of the object is desired.

DETAILED DESCRIPTION OF A PREFERRED EMBODIMENT

As noted above, for scanning based on reflected projected patterns to be successful, the scanning requires that the surface of the scanned object allow for good reflectivity in order for the scan to capture the image. Presently, tooth surfaces are difficult to scan in vivo because of their translucency, which causes scattering and poor image acquisition. The same holds true for brackets, crowns and other anatomical structures including gingival tissue. Successful scanning demands that translucent surfaces such as teeth are opaqued to allow superior reflectivity. The present invention provides for methods of scanning such objects in a wet-field environment, where liquid such as water or saliva is present on the object to be scanned.

Whereas the prior art went to great lengths to insure that any opaquing formulation was applied in a dry field environment, such as the $TiO_2$ powder mentioned previously, we have come to the realization that wet-field scanning is indeed possible, and even practical. In a first aspect, we provide for scanning the surface of an object in which moisture such as saliva or water is present on the surface. The method comprises the steps a) applying a saliva and water-resistant composition to the surface, wherein the composition is characterized in that it does not readily wash off the surface after application of the composition to the surface in the presence of saliva or water; and b) scanning the surface having the composition applied with a scanner.

The method is preferably practiced with the additional step of allowing the composition to form a film covering said surface prior to the performance of step b), with the film being substantially opaque. The film may be dry, or, alternatively, wet in which case the formulation will typically have a sticky consistency.

In one possible embodiment, the composition comprises a liquid composition. The composition can be applied to the surface by means of a brushing, spraying, dipping, using compressed air, etc. Alternatively, the composition might comprises a powder, applied by any suitable technique including compressed air or using a brush.

The method is particularly suitable for preparing an anatomical structure of a human for scanning in a wet-field environment. For example, the anatomical structure may comprises oral structures such as lips, gingival tissue, teeth, etc. in vivo where saliva is present on such structures.

Representative presently preferred compositions for use in wet-field scanning are described below in detail. For a liquid composition, it has been found that a composition comprising a pigment, a binder for promoting the binding of the pigment to the surface, and a liquid base for the pigment and binder is satisfactory. The base preferably comprises an alcohol to promote fast drying of the composition and the binder preferably comprises a composition of matter having a tendency to either harden or become sticky in the presence of saliva or water. One suitable binder is a denture adhesive, ground to a powder and mixed with the base. The pigment and binder could be dissolved completely in the base, or, alternatively, the pigment and binder could be suspended in the base in which case the pigment and binder float or are otherwise suspended in the base. In the latter situation, the composition is shaken well prior to use to insure an even application of the binder and pigment to the surface to be scanned.

The liquid opaquing composition could take a variety of forms, including an emulsion, a suspension, or a formulation in which the pigment and binder are dissolved completely in the base. What is important is that the formulation meet the basic requirements of a) capable of being applied to the surface of an object to be scanned, b) at least temporarily resistant to being washed off the surface due to the presence of water and saliva on the surface, and c) that improve the reflective properties of the surface, such as by providing an opaque film covering the object.

Representative Formulations

A representative formulation is described herein that is considered superior in terms of functionality and ease of use as compared to a prior art $TiO_2$-based aerosol powder formulation. The formulation comprises a liquid phase, biologically compatible composition that includes 1) a liquid base, such as a liquid alcohol base, e.g. dehydrated ethyl alcohol, 2) a pigment such as $TiO_2$, and 3) a binder that is resistant to water and saliva, that is, tends to harden, become sticky, or otherwise not wash off the surface to be scanned when water or saliva is present. It has been found that off-the-shelf denture adhesives (e.g., FIX-O-DENT™) in powdered form is a suitable binder for intra-oral scanning. Alternatively, and equivalently, the active ingredient in a denture adhesive that tends to harden or become sticky in the presence of water or saliva could be used. The base provides a solvent or volatile carrier for the binder and the pigment when they are initially in a powdered form. Alternatively, the base provides a medium for the binder and pigment to be suspended. The composition, when applied to the teeth, or other oral structures in a wet-field environment, resists being washed off the teeth or other oral structures even in the presence of saliva or other moisture. The composition promotes rapid drying of the formulation or the formulation becoming sticky or semi-solid. Further, the composition is such that it enables an even application of the formulation to all the surface.

In a preferred embodiment, the base liquid (e.g. ethyl alcohol) is present in the formulation in the range of between 40 and 90 percent by weight. It is important that the base does not initiate the solidification process of the binder. Therefore, it must preferably contain no water at all, or virtually no water. We have found that dehydrated ethyl alcohol with a purity of 99.8% (=0.2% water) is sufficient to provide a reasonable shelf life with the opaquer only marginally starting to gelatinize. Typically, no better purity than 99.8% is commercially available.

The formulation includes an opaquing pigment, preferably white in color, such as, for example, $TiO_2$. Other pigments are possible, such as $ZnO_2$ and pigments having some tint or color. The reflective pigment is preferably present in the formulation in the range of between 5 and 50 percent by weight.

The binder is used for promoting good adhesion of the formulation to the surface of the object being scanned. Preferably, the binder hardens or becomes sticky when exposed to water or saliva, to thereby prevent the formulation from being washed off due to saliva. In particular, for in-vivo scanning tooth surfaces, the binder needs to provide good binding properties even in the presence of saliva. A suitable binder for scanning teeth or other oral structures is a denture adhesive such as an off-the-shelf denture adhesive, in powder form, that is mixed with the pigment and the alcohol base. The range for a binder in the formulation will vary depending on the nature of the object being scanned, and for example can be present in the range of between 0.25% and 30%. As noted above, a suitable binder is FIX-O-DENT™ denture adhesive, ground in a powdered form, dissolved or suspended in the alcohol base.

The formulation set forth below allows for good adherence to the tooth's surface, a uniform layer that does not obliterate dental and gingival anatomy, is quick setting, will not wash away with salvia, is easily removed through normal tooth brushing, is bio-compatible, is opaque and has the desired reflective properties, will not degrade, and has a good shelf life. It does not require a complete drying of the teeth prior to application.

A presently preferred embodiment of an opaquing formulation for scanning is as follows:

| Percent (by weight) Range | Preferred valued for scanning teeth | Description |
| --- | --- | --- |
| 40%–94% | 81.5% ± 1% | Base: Dehydrated Ethyl Alcohol, 99.8% |
| 5%–50% | 15.5% ± 1% | Pigment: Titanium Dioxide |
| .25%–30% | 3% ± ½% | Binder (Denture Adhesive): Calcium/Zinc Polyvinyl Methyl Ether Maleate, Cellulose Gum, Silica, Peppermint Oil |

The above formulation is a white, biocompatible opaque liquid at room temperature.

The formulation is preferably applied by brushing the formulation onto the teeth. The formulation can be spread around the teeth and into crevices between teeth by gentle application of compressed air. The formulation dries quickly to a film due to the significant presence of alcohol in the formulation. The presence of alcohol in the formulation also insures that the formulation is readily spread evenly without smearing and excess localized build-up, and does not build up a crust on the surface of the teeth. The binder in the formulation also insures that the formulation is not washed off the teeth by the patient's saliva, and furthermore the formulation can be applied to teeth that are already moist with saliva. The formulation, which dries rapidly to a film, has a high degree of reflectivity to radiation in the visible portion of the spectrum due to the presence of the pigment in the formulation.

The formulation can be applied to other anatomical structures that need to be scanned besides oral structures. For example, the formulation could be applied to the nose, hand, or internal organs or bones during a surgical procedure to enable scanning of such structure. In such embodiments, the ratio of ingredients in the composition may be expected to vary. For example, in scanning objects that are not wet or likely to be wet or influenced by saliva, the risk of washing away of the solution is reduced and a different choice for binder material can be made.

Thus, we have invented a method of scanning the surface of an object in a wet-field environment comprising the steps of 1) applying a biocompatible, saliva and water-resistant composition to the surface such that the composition does not tend to be washed off the surface in the presence of water or saliva; 2) allowing the composition to dry to a film covering the surface with the film exhibiting opaque properties to improve the ability of the object to be scanned; and 3) scanning the surface having the film with a scanner. The object in one possible embodiment may be an anatomical structure of a human, such as an oral structure (e.g., teeth, gingival tissue).

In yet another aspect, we have invented a method of in-vivo scanning of an anatomical structure of a human comprising the steps of: applying a biocompatible, saliva and water-resistant composition to the surface of the anatomical structure, wherein said composition comprises a base, a pigment and a binder composed of a material having a tendency to harden or become sticky in the presence of water or saliva and thereby not be washed off the surface of the anatomical structure; allowing the liquid solution to dry to a film covering said surface of the anatomical structure with the film having a high degree of reflectivity of radiation; and scanning the surface having the film with a scanner.

As noted above, the invention is particularly suitable for use with scanning devices projecting a coded projection pattern onto the object and capturing the reflected pattern with an electronic imaging device (CCD camera). However, the improvements provided by this invention can be used in conjunction with other types of scanners.

The manner of application of the liquid opaquing solution to the surface to be scanned can vary from the preferred method of brushing. For example, the solution could be sprayed on using a spray container or other mechanical spray device. Alternatively, the object could be dipped in the solution.

In yet another alternative embodiment, a powdered pigment and powdered binder may be combined in a suitable proportion and mixed together (and possibly mixed with other ingredients) to form a powdered opaquing composition that works in a wet field environment. In this instance, there is no base liquid. The powdered formulation is applied by brushing, spraying or other suitable technique to the moist anatomical structures. The formulation temporarily resists being washed off the anatomical structure due to the presence of the binder in the formulation. The powder forms a film covering the anatomical structures which increases the opacity of the structure and allows it to be scanned successfully.

It is fully expected that persons skilled in the art will be able to derive other suitable opaquing compositions for application to surfaces in a wet-field environment from the present disclosure. The usage of such additional formulations for wet-field scanning is contemplated as being within the scope of the appended claims.

What is claimed is:

1. A method of scanning the surface of an object in which moisture such as saliva or water is present on said surface, comprising the steps of:

a) applying a liquid composition to said surface, wherein said liquid composition comprises a liquid base, a pigment, and a binder for promoting the binding of said pigment to said surface, wherein said binder comprises a material in a powder form suspended in said base and having a tendency to harden or become sticky in the presence of saliva or water, and wherein said liquid base comprises a substantially non-aqueous liquid thereby not initiating the solidification process of said binder; and b) scanning said surface having said liquid composition applied thereto with a scanner.

2. The method of claim 1, wherein said liquid composition form enables an even application of said liquid composition forming a uniform layer covering said surface, said uniform layer being substantially opaque.

3. The method of claim 1, wherein said object comprises an anatomical structure of a human.

4. The method of claim 3, wherein said anatomical structure comprises an oral structure.

5. The method of claim 4, wherein said oral structure comprises teeth.

6. The method of claim 1, wherein said liquid base comprises a dehydrated ethyl alcohol having 99.8% purity.

7. The method of claim 6, wherein said liquid base is present in an amount of 81.5%±1%, said pigment is present in an amount of 15.5%±1%, and said denture adhesive is present in an amount of 3%±½%, by weight.

8. A method of in-vivo scanning of an anatomical structure of a human in a wet-field environment, comprising the steps of:

applying a biocompatible, liquid composition to the surface of said anatomical structure, wherein said liquid composition comprises a volatile liquid base, a pigment and a binder composed of a material in a powder form suspended in said base and having a tendency to harden or become sticky in the presence of water or saliva and wherein said volatile liquid base comprises a substantially non-aqueous liquid thereby not initiating the solidification process of said binder; and scanning said surface having said liquid composition applied thereto with a scanner.

9. The method of claim 8, wherein said anatomical structure comprises an oral structure.

10. The method of claim 8, wherein said volatile liquid comprises a dehydrated alcohol having 99.8% purity present in an amount of between 40 and 94% by weight and wherein said denture adhesive is present in an amount of between 0.25% and 30% by weight.

11. The method of claim 8, wherein said liquid composition enables an even application of said liquid composition forming a uniform layer covering said surface of said anatomical structure, said uniform layer being substantially opaque.

12. An opaquing fluid for application to a surface of an object in preparation for scanning of the object, comprising, in combination:

a biocompatible, fluid comprising a mixture of a liquid base, a pigment, and a binder for promoting the binding of said base and said pigment to said surface, wherein said binder comprises a composition of matter in a powder form suspended in said base, wherein said binder tends to harden or become sticky in the presence of saliva or water, wherein said binder is an active ingredient of a denture adhesive, wherein said base comprises a substantially non-aqueous liquid thereby not initiating the solidification process of said binder; and wherein said fluid, after application to said surface, forms an uniform layer covering said surface with said uniform layer being substantially opaque.

13. The fluid of claim 12, wherein said base comprises a volatile liquid.

14. The fluid of claim 13, wherein said volatile liquid is present in an amount of between 40% and 94% by weight and wherein said denture adhesive is present in an amount of between 0.25% and 30% by weight.

* * * * *